US008925366B2

(12) United States Patent
Mulhern (10) Patent No.: US 8,925,366 B2
(45) Date of Patent: Jan. 6, 2015

(54) GAS EQUILIBRIUM COIL FOR PROVIDING, IN REAL-TIME, A GAS CALIBRATING SOLUTION

(71) Applicant: Nova Biomedical Corporation, Waltham, MA (US)

(72) Inventor: Edward J. Mulhern, Wayland, MA (US)

(73) Assignee: Nova Biomedical Corporation, Waltham, MA (US)

( * ) Notice: Subject to any disclaimer, the term of this patent is extended or adjusted under 35 U.S.C. 154(b) by 178 days.

(21) Appl. No.: 13/626,143

(22) Filed: Sep. 25, 2012

(65) Prior Publication Data
US 2014/0083157 A1 Mar. 27, 2014

(51) Int. Cl.
*G01N 33/00* (2006.01)

(52) U.S. Cl.
USPC .......................................... 73/1.06

(58) Field of Classification Search
USPC .............................. 436/11; 73/1.06
See application file for complete search history.

(56) References Cited

U.S. PATENT DOCUMENTS

| | | | |
|---|---|---|---|
| 4,151,108 A | 4/1979 | Sorensen et al. | |
| 4,289,648 A | 9/1981 | Hoskins et al. | |
| 4,301,117 A * | 11/1981 | Smernoff | 422/549 |
| 4,336,031 A | 6/1982 | Hopmeier et al. | |
| 4,369,127 A | 1/1983 | Cormier et al. | |
| 4,424,276 A * | 1/1984 | Clark et al. | 205/777.5 |
| 4,567,748 A * | 2/1986 | Klass et al. | 73/1.05 |
| 4,600,697 A | 7/1986 | Smernoff | |
| 4,843,013 A | 6/1989 | Chiang | |
| 5,070,023 A * | 12/1991 | Calabrese | 436/8 |
| 5,204,266 A * | 4/1993 | Calzi | 436/11 |
| 5,493,891 A * | 2/1996 | Slemeyer | 73/1.06 |
| 5,578,194 A | 11/1996 | Young et al. | |
| 5,885,533 A | 3/1999 | Savage et al. | |
| 5,902,751 A | 5/1999 | Godec et al. | |
| 5,913,232 A | 6/1999 | Betts et al. | |
| 6,066,249 A | 5/2000 | Manzoni et al. | |
| 7,255,332 B2 * | 8/2007 | Osborn et al. | 261/28 |

FOREIGN PATENT DOCUMENTS

EP 0508761 A2 10/1992
WO 94/16323 A1 7/1994

OTHER PUBLICATIONS

PCT International Search Report and Written Opinion for PCT/US2013/057202 mailed Nov. 26, 2013.

* cited by examiner

*Primary Examiner* — Hezron E Williams
*Assistant Examiner* — Mark A Shabman
(74) *Attorney, Agent, or Firm* — Robert R. Deleault, Esq.; Mesmer & Deleault, PLLC (57) ABSTRACT

A gas-solution equilibrium device for a liquid sample gas analyzer includes a temperature-controlled, thermally-conductive mandrel, a coil of gas-permeable tubing wrapped around the mandrel, the gas-permeable tubing having an inlet and an outlet, and a housing having an internal space containing the temperature-controlled, thermally-conductive mandrel, the coil of gas-permeable tubing and a volume of gas where the gas-permeable tubing has a predefined linear length and a predefined wall thickness, the combination of which together is capable of equilibrating a liquid passing through the coil at a predefined flow rate with oxygen in the atmosphere to provide a gas calibration solution in real time at the outlet of the tubing for the liquid gas analyzer.

23 Claims, 6 Drawing Sheets

GAS EQUILIBRIUM COIL FOR PROVIDING, IN REAL-TIME, A GAS CALIBRATING SOLUTION

BACKGROUND OF THE INVENTION

1. Field of the Invention

The present invention relates generally to calibration standards for electrodes. Particularly, the present invention relates to gas control liquids for quality control and/or calibration of gas analyzer equipment such as blood gas analyzers and water gas analyzers.

2. Description of the Prior Art

Various fluid analysis devices are used in testing and measuring gas and/or electrolyte levels in fluids. These devices are used, for example, in medical and environmental applications to measure the gas and/or electrolyte levels in blood, urine, water, and other fluids.

Fluid analysis devices must be calibrated frequently when used to test fluid samples. It is common practice to utilize control solutions for verifying the accuracy and reliability of these analysis devices. For example, blood gas analyzers typically include electrodes that measure pH, the partial pressure of carbon dioxide ($pCO_2$) and the partial pressure of oxygen ($pO_2$) of a blood sample. Such electrodes are typically calibrated prior to use for measuring a blood sample.

Calibration of an electrode involves contacting the electrode with standard solutions or gases having known concentrations of the substance being analyzed. The electrode provides an electrical response that is used to generate a calibration slope. The electrode then is contacted with the sample to be measured, which generates a further electrical response. The calibration slope is used to convert the electrical response into the concentration of the substance in the sample. For example, electrodes in blood gas analyzers are calibrated periodically because the response provided by an electrode for a particular sample tends to drift (i.e. vary) with the passing of time.

Typically, a reference or calibration container holds a reference or calibration solution that contains gases, such as oxygen and carbon dioxide, in solution at known partial pressures. Because these partial pressures are known to a relatively precise degree, the reference or calibration solution can be used to accurately calibrate the fluid analysis machine after fluid samples have been tested.

Gas tonometered aqueous solutions packaged in sealed containers have been used as calibration standards for oxygen and carbon dioxide electrodes. The manufacturing environment for the gas tonometered solutions requires precise temperature and pressure control to ensure the accuracy of the calibration standards. It is also necessary to equilibrate these tonometered solutions to a known temperature before using them to calibrate the electrodes in the analyzer.

Other liquid gas control products have been proposed which are based on components of human blood or components proposed for use as blood substitutes such as fluorocarbon and silicone compound emulsions.

Some control/calibration solutions have been provided in gas-tight, sealed ampuls and contain known concentrations of dissolved oxygen and carbon dioxide.

Analyzers such as, for example, blood gas analyzers use various methods of packaging calibration fluids so that dissolved gas levels are stable over a period of time; typically, the shelf life of these calibration fluids are eighteen (18) months or more. Bag/container materials and fitments for accessing the contents of the bag/container are selected to minimize gas diffusion either into or out of the bag/container depending on various factors such as atmospheric pressure and temperature.

SUMMARY OF THE INVENTION

The prior art calibration and/or control solutions suffer from various disadvantages. For example, commercially available and prepared aqueous gas control liquids adequately mimic given levels of blood for pH and $pCO2$ but do not have adequate oxygen buffering capacity as they are unable to dissolve an adequate amount of oxygen. Such controls are prone to inaccuracy in the presence of relatively small amounts of outside oxygen contamination and may also falsely indicate certain types of instrument malfunctions.

Emulsion-based calibration/control solutions have a disadvantage where bubbles in the measuring chambers of the analyzer equipment create cleaning difficulties and cause control-to-sample carry over. Preparing control samples at the time of calibration has its own disadvantages. This gives rise to problems involving extraordinarily much labor, expensive extra equipment and uncertainty since the preparation process is technically rather complicated.

Materials and fitments used in containers for calibration solutions designed to minimize gas diffusion also suffer disadvantages. Keeping oxygen at a stable level in a calibration pack over long periods of time is particularly challenging, especially when the differences in equilibrium between the atmosphere and the stored reagent may be great. In addition, the reactivity of oxygen to the container material or the reagents is also quite challenging.

It is an object of the present invention to provide a non-premade and non-prepackaged gas calibration standard in a liquid reagent and/or calibration/standard solution for use in a gas-liquid analyzer.

The present invention achieves these and other objectives by providing a device capable of driving dissolved gas values in a liquid reagent and/or calibration/standard solution to a controlled level in real-time for the purpose of using the reagent or liquid for gas calibration purposes.

In broad terms, the present invention employs a long, thin-walled, gas permeable tubing wrapped around a heated, temperature-controlled mandrel held at an elevated temperature such as, for example, 37° C.; also called a gas-liquid equilibrium coil for providing, in real-time, a gas calibrating solution for use in a gas liquid analyzer. The gas environment immediately surrounding the mandrel and tubing is also closely controlled with respect to temperature and gas concentration. One example of an easily available and inexpensive gas usable in the present invention is atmospheric air. The tubing material is selected for high gas permeability such as, for example, high oxygen permeability. When a reagent and/or calibration solution is passed through the coil at elevated temperature, the reagent and/or calibration solution rapidly assumes a new equilibrium based on atmospheric pressure, temperature and percent of gas in the space surrounding the coil. By knowing the exact atmospheric pressure or the gas pressure within the chamber in which the mandrel and tubing are located, the exact gas value at that moment can be calculated and, thus, can be used for calibration purposes.

The wall thickness of the gas permeable tubing is a compromise between thinner being better for gas diffusion and wall collapse under vacuum caused by a peristaltic pump. The combination of material, temperature and vacuum defines the parameters for determining a usable wall thickness. The internal diameter of the gas permeable tubing is a compromise between larger being better for head loss under vacuum caused by the peristaltic pump and smaller being better for surface area exposed per given volume. Of all the variables (i.e. tube material, thickness, length of tubing, dwell time of solution in the tubing, temperature, etc.), temperature is the first order effect. At low temperatures, equilibrium is achieved very slowly, because diffusion is temperature dependent. Various fluids were tested with gas values as low as 100 mm Hg and as high as 220 mm Hg and were driven to equilibrium at a given temperature. Lower temperatures took much longer but higher temperatures were quick.

In one embodiment of the present invention, the gas-solution equilibrium device for a liquid sample gas analyzer includes a temperature-controlled, thermally-conductive mandrel, a coil of gas-permeable tubing wrapped around the mandrel, the gas-permeable tubing having an inlet and an outlet, and a housing having an internal space in equilibrium with a gas atmosphere containing the temperature-controlled, thermally-conductive mandrel and the coil of gas-permeable tubing. The coil of gas-permeable tubing has a predefined linear length and the gas-permeable tubing has a predefined wall thickness where the combination of which together is capable of equilibrating a liquid passing through the coil at a predefined flow rate with a gas within the housing to provide an gas calibration solution at the outlet of the tubing for the liquid gas analyzer.

In another embodiment of the present invention, the gas within the housing is atmospheric oxygen and the housing has openings for facilitating equilibration between the internal space within the housing and the atmosphere.

In another embodiment of the present invention, the gas-permeable tubing is made of a material having relatively high gas permeability for oxygen or carbon dioxide in the range of about $0.6 \times 10^{-13}$ $cm^3 \cdot cm$ $cm^{-2}$ $s^{-1}$ $Pa^{-1}$ to about $10 \times 10^{-13}$ $cm^3 \cdot cm$ $cm^{-2}$ $s^{-1}$ $Pa^{-1}$ at 25° C. for a 25 micron thick film. It is noted that the gas permeability specification of the tubing material is used as an indicator of the type of tubing usable in the present invention. If a particular material has a gas permeability value at 25° C. for a 25 micron film within or close to the specified range, then tubing make of that particular material would be usable in the present invention. For purposes of this specification and claims, all permeability values are values for a 25 micron film at 25° C.

In a further embodiment of the present invention, the gas-permeable tubing is made of a material having an oxygen permeability equal to or greater than about $0.6 \times 10^{-13}$ $cm^3 \cdot cm$ $cm^{-2}$ $s^{-1}$ $Pa^{-1}$, preferably equal to or greater than about $3 \times 10^{-13}$ $cm^3 \cdot cm$ $cm^{-2}$ $s^{-1}$ $Pa^{-1}$ and, more preferably equal to or greater that $7 \times 10^{-13}$ $cm^3 \cdot cm$ $cm^{-2}$ $s^{-1}$ $Pa^{-1}$.

In still a further embodiment of the present invention, the gas-permeable tubing is made of a material having an oxygen permeability equal to about $3 \times 10^{-13}$ $cm^3 \cdot cm$ $cm^{-2}$ $s^{-1}$ $Pa^{-1}$.

In yet another embodiment of the present invention, the gas-permeable tubing is made of a material having oxygen permeability in the range of about $3 \times 10^{-13}$ $cm^3 \cdot cm$ $cm^{-2}$ $s^{-1}$ $Pa^{-1}$ to about $7 \times 10^{-13}$ $cm^3 \cdot cm$ $cm^{-2}$ $s^{-1}$ $Pa^{-1}$.

In another embodiment of the present invention, the gas-permeable tubing has a wall thickness in the range of about 0.011 inches to about 0.014 inches and, preferably, in the range of about 0.012 inches to about 0.013 inches.

In another embodiment of the present invention, the gas-permeable tubing has a wall thickness sufficient to prevent wall collapse when the tubing is subjected to a vacuum effect from a peristaltic pump while providing sufficient oxygen permeability to achieve solution oxygen equilibrium with atmospheric oxygen at the solution outlet for a solution passing through the tubing.

In a further embodiment of the present invention, the gas-permeable tubing is made of a material having carbon dioxide permeability in the range of about $3 \times 10^{-13}$ $cm^3 \cdot cm$ $cm^{-2}$ $s^{-1}$ $Pa^{-1}$ to about $10 \times 10^{-13}$ $cm^3 \cdot cm$ $cm^{-2}$ $s^{-1}$ $Pa^{-1}$.

In still a further embodiment of the present invention, the gas-permeable tubing is made of a material having a carbon dioxide permeability equal to or greater than about $3 \times 10^{-13}$ $cm^3 \cdot cm$ $cm^{-2}$ $s^{-1}$ $Pa^{-1}$, preferably equal to or greater than about $7 \times 10^{-13}$ $cm^3 \cdot cm$ $cm^{-2}$ $s^{-1}$ $Pa^{-1}$ and, more preferably equal to or greater than $10 \times 10^{-13}$ $cm^3 \cdot cm$ $cm^{-2}$ $s^{-1}$ $Pa^{-1}$.

In another embodiment, the temperature-controlled, thermally-conductive mandrel has a thin-film, resistive heater disposed on an inside wall of the mandrel, or an outside wall of the mandrel, or both. The resistive heater may also employ heating coils within a tubular mandrel instead of a thin-film heater. The heating mechanism employed to heat the mandrel may use other methods besides resistive heating such as, for example, thermoelectrics (i.e. based on the Peltier effect), heated circulating fluids that circulate through the mandrel, and the like.

In still another embodiment, the gas-permeable tubing has a length in the range of about 35 inches to about 75 inches.

In yet another embodiment, the coil has predefined number of turns in the range of about 11 turns to about 23 turns.

In another embodiment, the gas-permeable tubing is made of a material selected from the group consisting of polytetrafluoroethylene (PTFE), fluorinated ethylene propylene (FEP), perfluoroalkoxy copolymer such as tetrafluoroethylene-perfluoro(alkoxy vinyl ether) film (PFA), and ethylene-tetrafluoroethylene copolymer suchs as polyethylenetetrafluoroethylene (ETFE).

In another embodiment, there is disclosed a method of providing, in real-time, a gas calibration solution for a liquid sample gas analyzer. The method includes setting a temperature-controlled, thermally conductive mandrel to a predefined temperature and moving a calibrating solution at a predefined flow rate through a coil of gas-permeable tubing wrapped around the temperature-controlled, thermally conductive mandrel where the gas-permeable tubing has a predefined length and a predefined wall thickness, is exposed to an atmosphere of a predefined gas and is made of a material having relatively high permeability for the predefined gas. The calibrating solution has a gas content in equilibrium with the predefined gas at an outlet of the gas-permeable tubing.

In another embodiment, the method includes enclosing the temperature-controlled, thermally-conductive mandrel and the coil of gas-permeable tubing within a housing having a housing inlet connected to an inlet of the gas-permeable tubing and a housing outlet connected to the outlet of the gas-permeable tubing.

In a further embodiment, the method includes determining the gas concentration of the calibrating solution at the outlet of the gas-permeable tubing based on the then known atmospheric pressure, the temperature of the mandrel and the percent of predefined gas.

In another embodiment, the method includes selecting a gas-permeable tubing having an oxygen permeability in the range of about $3 \times 10^{-13}$ $cm^3 \cdot cm$ $cm^{-2}$ $s^{-1}$ $Pa^{-1}$ to about $7 \times 10^{-13}$ $cm^3 \cdot cm$ $cm^{-2}$ $s^{-1}$ $Pa^{-1}$.

In still another embodiment, the method includes selecting gas-permeable tubing having a wall thickness sufficient to prevent wall collapse when the tubing is subjected to a vacuum effect from a peristaltic pump while providing sufficient oxygen permeability to achieve solution oxygen equilibrium with atmospheric oxygen at the outlet for the calibrating solution passing through the tubing.

In another embodiment, the method includes selecting gas-permeable tubing made of a material selected from the group consisting of polytetrafluoroethylene (PTFE), fluorinated ethylene propylene (FEP), perfluoroalkoxy copolymer such as tetrafluoroethylene-perfluoro(alkoxy vinyl ether) film (PFA), and ethylene-tetrafluoroethylene copolymer suchs as polyethylenetetrafluoroethylene (ETFE).

In a further embodiment of the present invention, a gas-liquid equilibrium coil where the gas-liquid equilibrium coil provides, in real-time, a gas calibrating solution in a gas-liquid analyzer is presented. The gas-liquid equilibrium coil includes a temperature-controlled, thermally-conductive mandrel, a coil of gas-permeable tubing wrapped around the mandrel, the gas-permeable tubing having an inlet and an outlet, and temperature and gas means for controlling the environment around the gas-liquid equilibrium coil wherein a gas calibrating solution that exits the gas-liquid equilibrium coil has a predefined gas concentration defined by the temperature and gas means.

DETAILED DESCRIPTION OF THE PREFERRED EMBODIMENT

Figure 1:
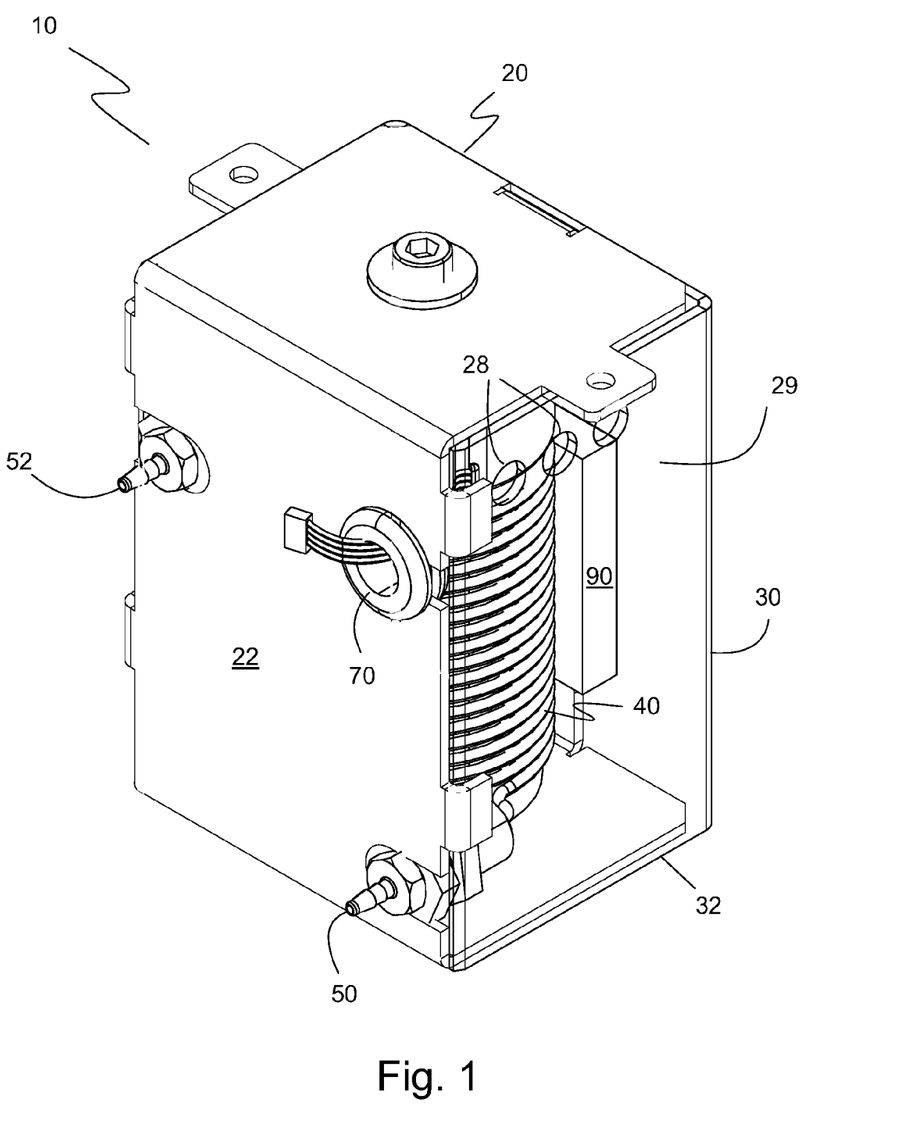
FIG. 1 is a rear, perspective view of one embodiment of the present invention showing a housing containing a gas equilibration device that includes a coil of gas-permeable tubing and a mandrel.

The preferred embodiments of the present invention are illustrated in FIGS. 1-9. FIG. 1 shows one embodiment of a gas-liquid equalizer assembly 10 of the present invention. Gas-liquid equalizer assembly 10 includes a housing 20 that includes a frame 22 and a cover 30 forming an internal space 29. Within internal space 29 of housing 20 is a gas equilibration device 40. Gas equilibration device 40 is used to provide gas calibration solution formed in real-time to a liquid gas analyzer. Gas-liquid equalizer assembly 10 also includes a solution inlet 50, a solution outlet 52 and a heater cable port 70. In an embodiment of cover 30 that uses atmospheric oxygen as the gas standard, such embodiment typically includes vent openings 28 to permit equilibrium of air between internal space 29 and the atmosphere.

Figure 2:
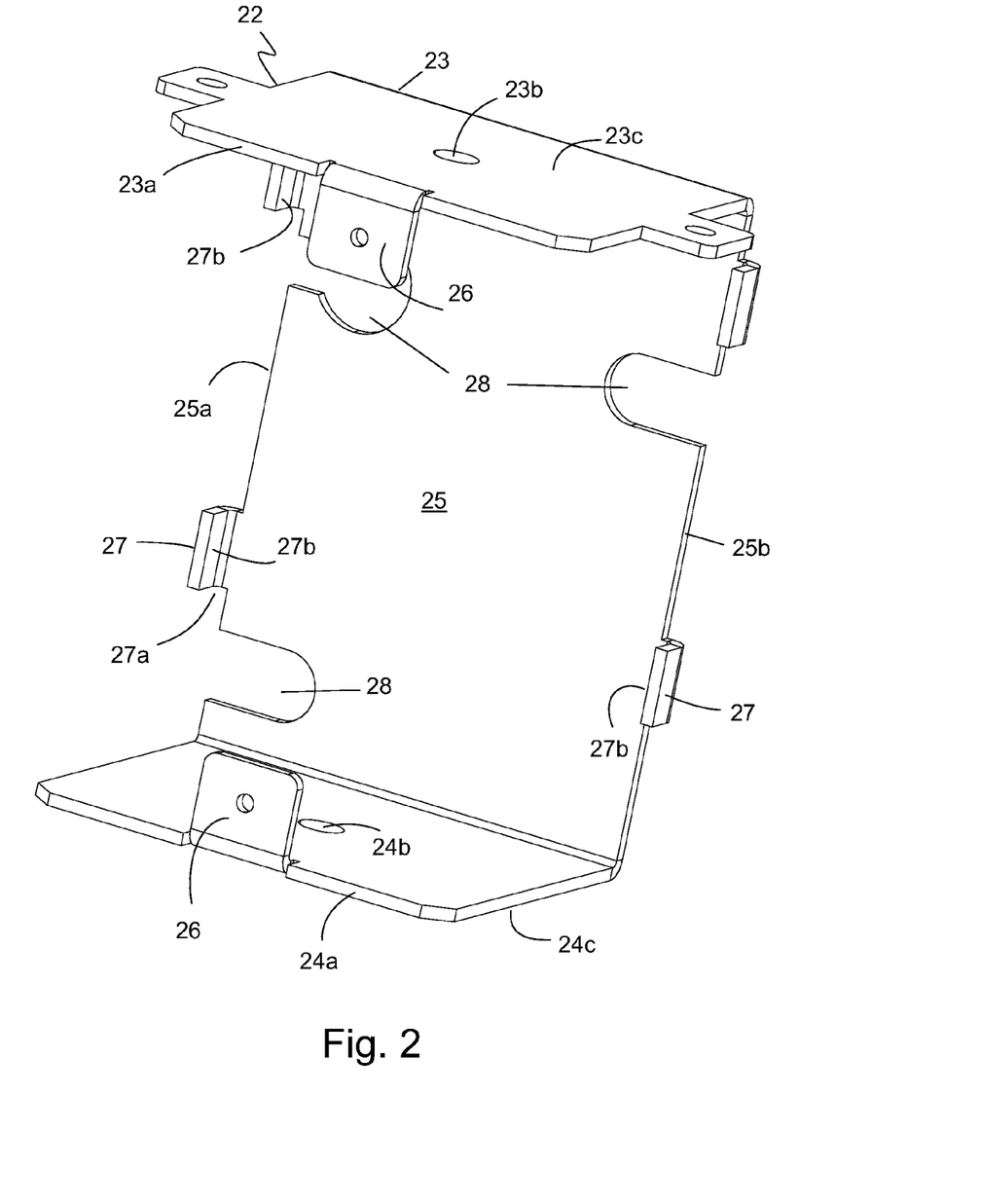
FIG. 2 is a front perspective view of one embodiment of the frame shown in FIG. 1.

Turning now to FIG. 2, there is shown a front perspective view of frame 22. Frame 22 has a generally C-shape when viewed from the side with a frame top 23, a frame bottom 24 and a frame wall 25 that extends vertically between and directly connects to frame top 23 and frame bottom 24. Frame top 23 is spaced from and substantially parallel to frame bottom 24. Frame top 23 and frame bottom 24 support and anchor gas equilibration device 40 in a relatively fixed position. Extending substantially perpendicular towards each other from frame top 23 and frame bottom 24 are securing tabs 26. Securing tabs 26 extend from a peripheral edge 23a and 24a of frame top 23 and frame bottom 24, respectively, located opposite from frame wall 25. Securing tabs 26 are the points of attachment for securing cover 30 to frame 22. Frame wall 25 also optionally includes at least one flange 27 on opposite sides of frame 22. Flange 27 is transverse to and spaced from a wall first side edge 25a and a wall second side edge 25b. Each flange 27 forms a cover side receiving space 27a between first side edge 25a and second side edge 25b where the distance between an inside surface 27b of flange 27 and the respective first and second side edges 25a, 25b is slightly larger than the thickness of a cover sidewall 32 of cover 30 (shown in FIGS. 1 and 3), which helps hold cover 30 to frame 22. In the embodiment shown, each of frame top 23 and frame bottom 24 has a top aperture 23b and bottom aperture 24b, respectively, for receiving a fastener for anchoring the gas equilibration device 40 to frame 22. It is contemplated that gas equilibration device 40 may be anchored in other ways such as using rails, clips, recesses, and the like that would anchor the ends of the gas equilibration device 40 to frame top 23 and frame bottom 24 to prevent movement of gas equilibration device 40. Frame wall 25 may also include a plurality of openings and/or slots 28 to accommodate the tube fittings and heater cable of the gas equilibration device 40. Frame 22 is made of a rigid material and has sufficient strength to support and anchor gas equilibration device 40 and cover 30. Acceptable materials include metal, nonmetal, carbon composites, plastics, and the like.

Figure 3:
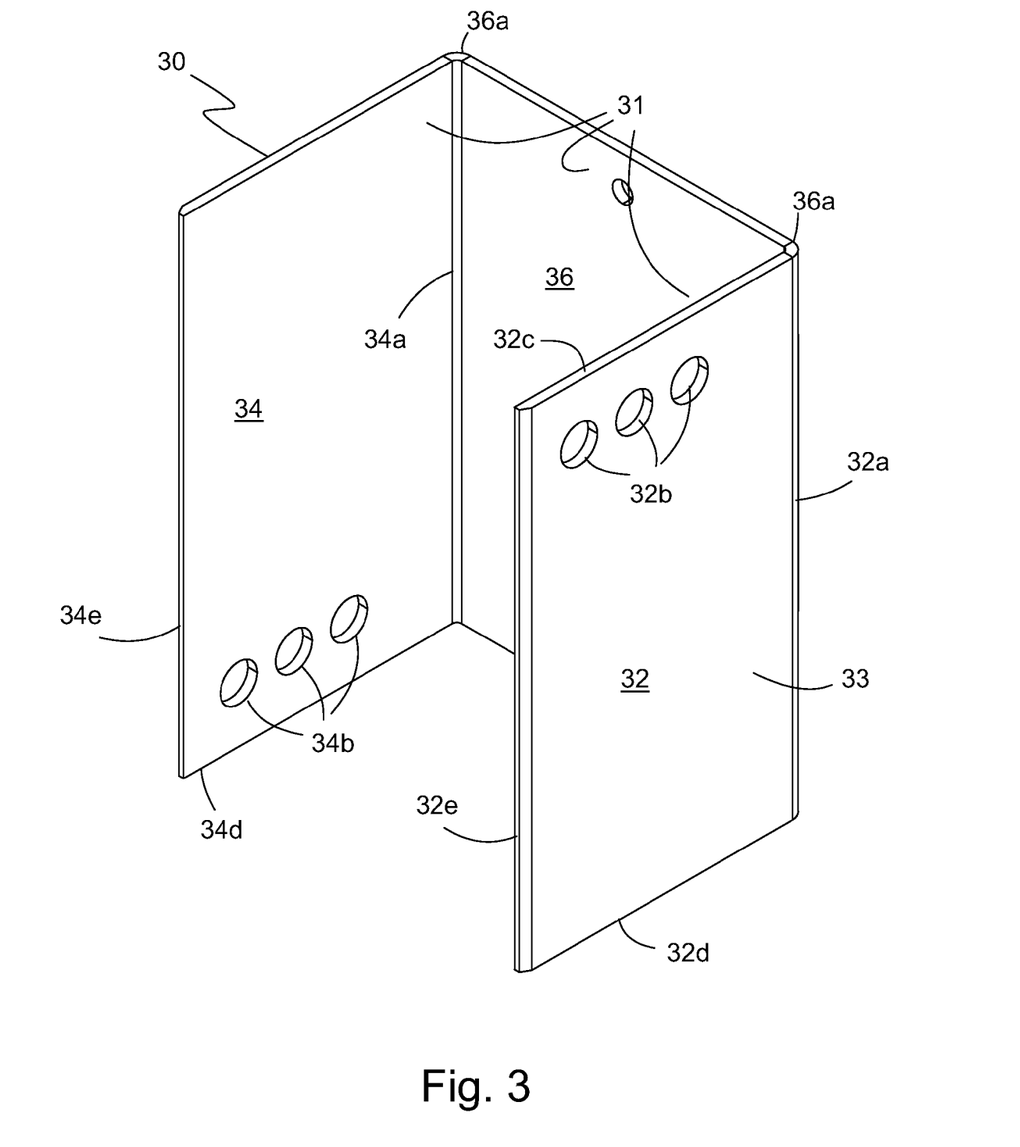
FIG. 3 is a rear, perspective view of one embodiment of the cover shown in FIG. 1.

FIG. 3 illustrates one embodiment of cover 30. In this embodiment, cover 30 has a pair of opposed cover side walls 32, 34 and a cover front wall 36. Cover front wall 36 is directly connected along opposed and parallel cover longitudinal edges 36a between cover side walls 32, 34 along cover side wall edges 32a, 34a. Each of cover side walls 32, 34 has one or more vent openings 32b, 34b through cover side walls 32, 34, respectively, when using atmospheric air for gas-solution equilibrium purposes. Preferably, vent openings 32b, 34b are spaced from the respective edges 32c, 34d to provide passive air flow in order to maintain equilibrium between the air within the internal space 29 between cover side walls 32, 34 and the atmosphere. The thickness of cover side walls 32, 34 and cover front wall 36 is selected to provide protection to gas equilibration device 40 from inadvertent damage. The longitudinal length of cover side walls 32, 34 and cover front wall 36 is preferably equal to the distance between the outside surfaces 23c, 24c of frame top 23 and frame bottom 24 so that the peripheral edges 23a, 24a of frame top 23 and frame bottom 24 provide a supporting surface for and against cover inside surface 31. Wall longitudinal edges 32e, 34e have a thickness that is slightly smaller than cover side receiving space 27a of frame 22 so that flange 27 of frame 22 provides an opposed surface (i.e. inside surface 27b) against a wall outside surface 33. Thus, frame top and bottom peripheral edges 23a, 24a prevent cover 30 from collapsing onto gas equilibration device 40 while flange 27 prevents cover side walls 32, 34 from separating away from frame top and bottom peripheral edges 23a, 24a. Although any material may be used for cover 30, the preferred material is a clear acrylic so that the solution flowing through gas equilibration device 40 may be viewed.

Figure 4:
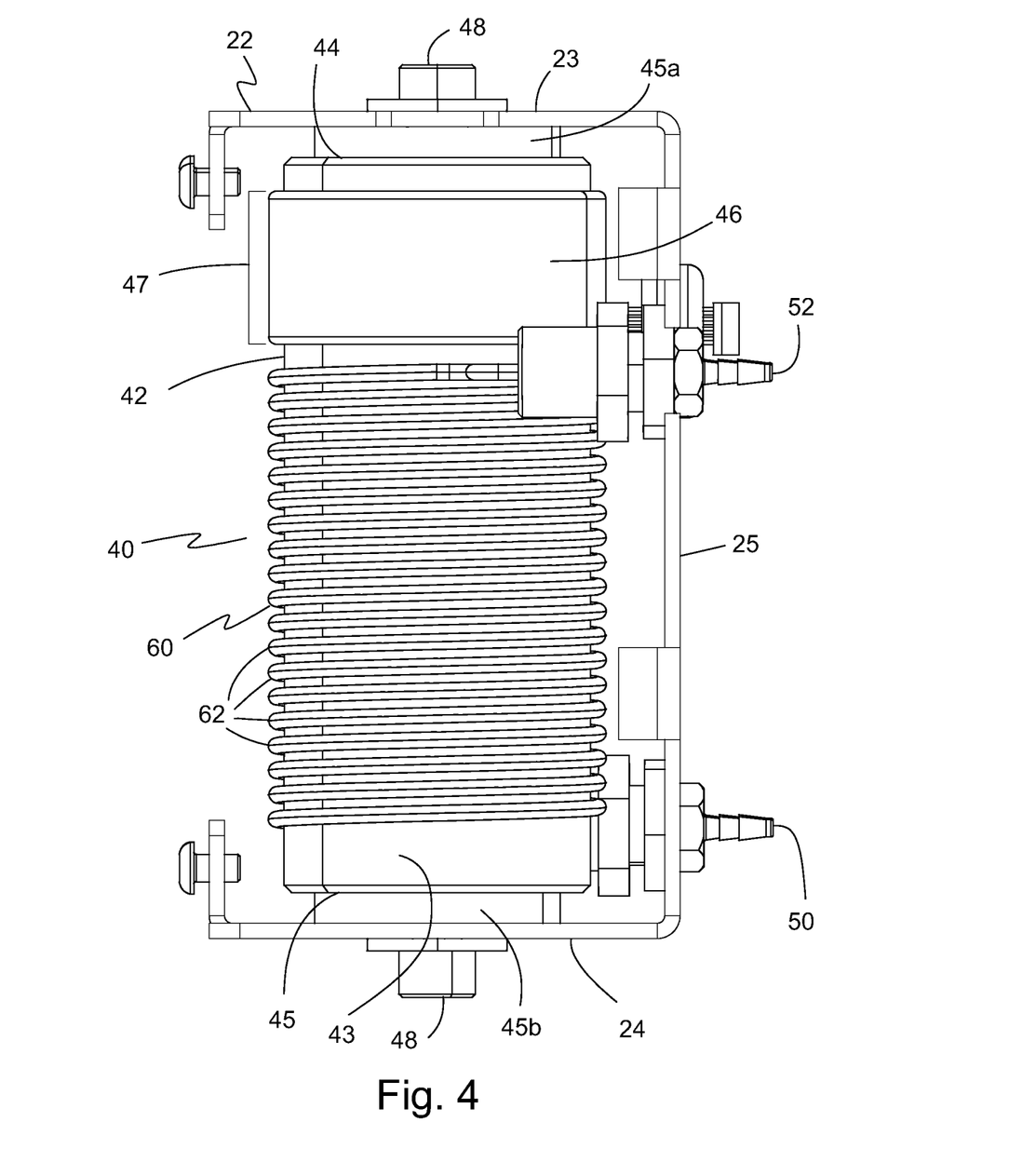
FIG. 4 is a left side plan view of the embodiment shown in FIG. 1 with the cover removed.

FIG. 4 is a side view of the gas-liquid equalizer assembly 10 with cover 30 removed. As shown, gas equilibration device 40 is secured at a top end 44 and a bottom end 45 to frame top 23 and frame bottom 24, respectively, of frame 22 using a fastener member 48. Gas equilibration device 40 includes a temperature-controlled, thermally-conductive mandrel 42 and a coil 60 of gas-permeable tubing wrapped around a mandrel outside surface 43 of mandrel 42. Coil 60 includes a plurality of spaced coil/tubing wraps 62 around mandrel 42 such that a majority of an outside surface of the gas-permeable tubing is exposed to the gas atmosphere (i.e. air or other predefined gas) around coil 60. Coil 60 has a first coil end 64 (not shown) connected to solution inlet 50 and a second coil end 66 (not shown) connected to solution outlet 52. In this embodiment of the present invention, solution inlet 50 and solution outlet 52 is characterized as a barb fitting, which is configured for connecting to other resilient tubing. Optionally, gas equilibration device 40 includes a mandrel insulator 46 at an upper end portion 47 to facilitate maintaining the temperature of the temperature-controlled mandrel 42. Gas equilibration device 40 may also optionally include insulating spacers 45a, 45b disposed between top and bottom ends 44, 45 of mandrel 42 and frame top and bottom 22, 24, respectively. Insulating spacers 45a, 45b also enhance temperature control by reducing heat conduction between gas equilibration device 40 and frame 22, especially when frame 22 is made of a thermally-conductive material such as, for example, metal. Other insulating components 90 (as shown in FIG. 1) such as a foam insulator block may optionally be included between gas equilibration device 40 and frame 22/cover 30 to further reduce heat loss from internal space 29.

Figure 5:
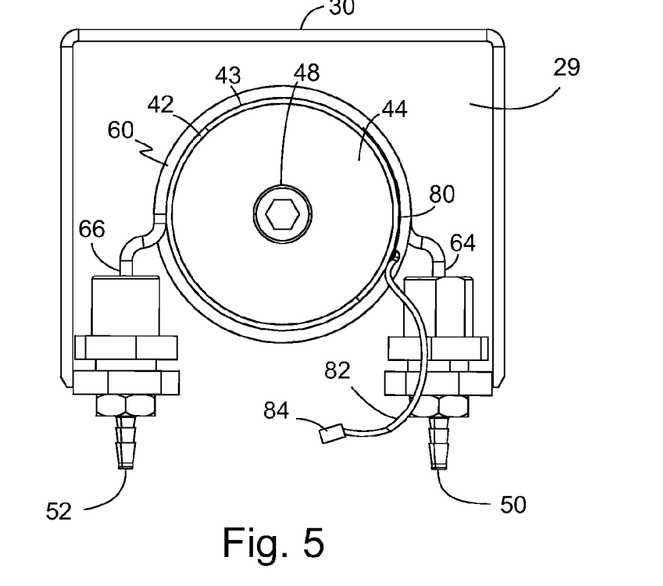
FIG. 5 is a top plan view of the embodiment shown in FIG. 1 with the frame removed.

Turning now to FIG. 5, there is illustrated a top view of the illustrated embodiment with frame 22 removed and showing gas equilibration device 40 disposed within internal space 29 created by cover 30 and frame 22. In this embodiment, temperature-controlled, thermally-conductive mandrel 42 includes a heater 80 in the form of a thin-film, flexible heater intimately connected to mandrel outer surface 43 between mandrel outer surface 43 and coil 60. It is contemplated that mandrel 42 may be solid or tubular and that heater 80 may also be intimately connected to an inside surface of a tubular mandrel 42 or may include heater coils or one or more thermoelectric modules disposed within a tubular mandrel 42. Heater 80 has an electrical lead 82 connected on one end to heater 80 and to an electrical connector 84 on an opposite end. It is also contemplated that the heating mechanism may use other methods besides resistive heating such as, for example, thermoelectrics (i.e. based on the Peltier effect), heated circulating fluids, and the like. An example of thermoelectrics would take advantage of the particular characteristics of thermoelectric modules. Thermoelectric modules are heat pumps with a hot side and a cold side. This system could be used to cool fluids back down to 37° C. after driving the equilibrium at temperatures of 40° to 42° C. Higher temperatures would provide lower $pO_2$ equilibrium values. The calibrating fluid would come out of the heated side of the thermoelectric module at some value of 100 to 140 mm $pO_2$. The calibrating fluid would then go into a gas tight tube made of a material such as saran or stainless steel and be cooled back down before going into the analyzer. Lower values of 100 to 150 mm might be more valuable since they are closer to the clinically relevant zone. A different embodiment would use the cold side to drive a high calibration value and the hot side to drive a low calibration value.

As seen in this view, first coil end 64 is connected to solution inlet 50 and second coil end 66 is connected to solution outlet 52 to provide continuous fluid communication through coil 60 and the remaining fluid-testing portion of a liquid-gas analyzer such as, for example, a blood gas analyzer or a water gas analyzer. Top end 44 of mandrel 42 includes fastener 48 that typically secures mandrel 42 to frame 22 through frame top 23. A similar arrangement is used to secure bottom end 45 to frame 22 through frame bottom 24.

Figure 6:
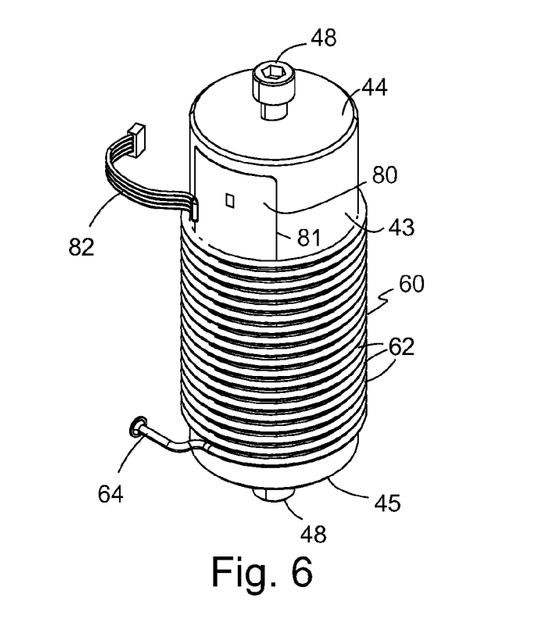
FIG. 6 is a perspective view of one embodiment of the present invention showing the mandrel, the heating member and the coil of gas-permeable tubing.

FIG. 6 is a perspective view of the gas equilibration device 40. As can be seen, heater 80 is disposed against mandrel outer surface 43 of mandrel 42. Coil 60 is relatively snugly wound around mandrel 42 and heater 80 over a major portion of mandrel outer surface 43 leaving sufficient access for electrical lead 82 of heater 80. Coil 60 has a plurality of coil/tubing wraps 62 that are spaced from each other as evidenced by a longitudinal heater edge 81 showing between each of coil wraps 62. First coil end 61 is spaced from mandrel 42 adjacent mandrel bottom end 45 to allow connecting to a solution inlet 50 such as a barb fitting.

Figure 7:
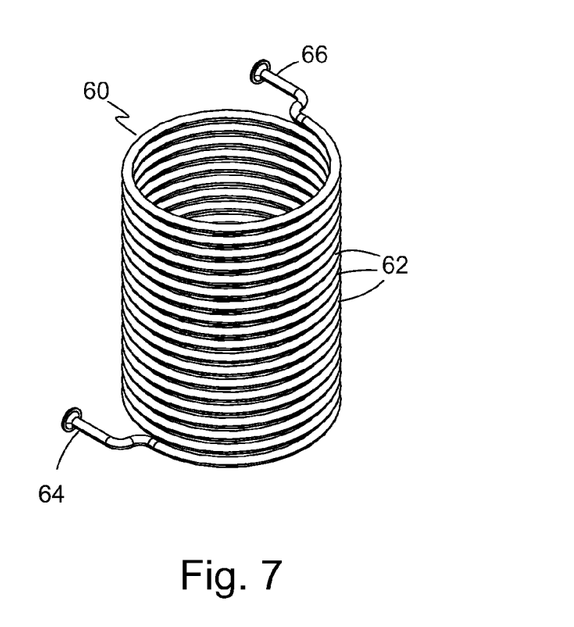
FIG. 7 is a perspective view of one embodiment of the coil of the gas equilibration device of the present invention shown in FIG. 1.
Figure 8:
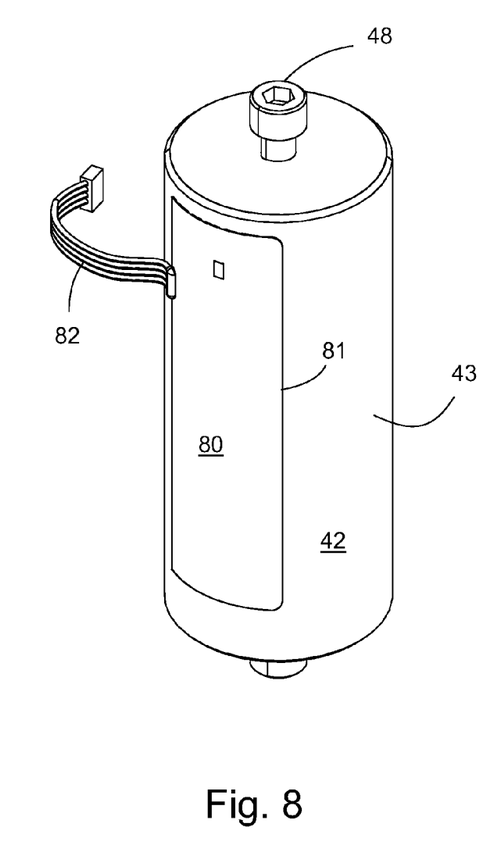
FIG. 8 is a perspective view of one embodiment of the mandrel and heating member of the present invention shown in FIG. 1.
Figure 9:
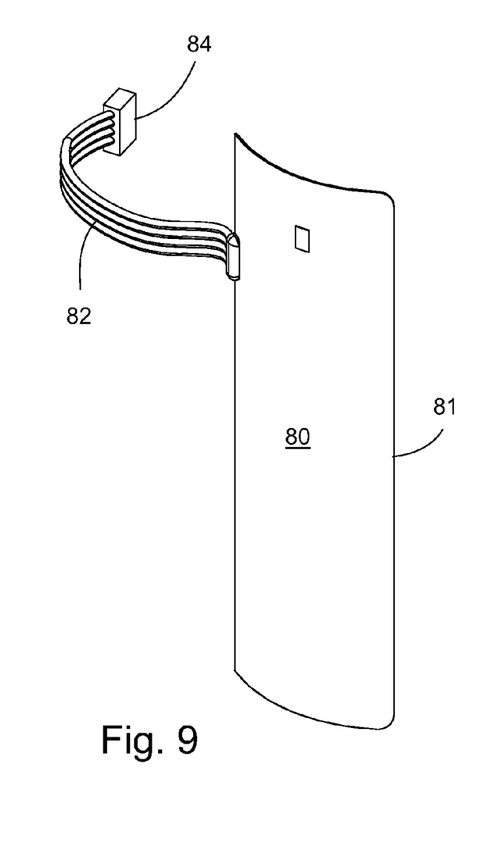
FIG. 9 is a perspective view of the heating member of the gas equilibration device shown in FIG. 6.

FIG. 7 shows only coil 60 with the plurality of coil wraps 62 between first coil end 64 and second coil end 66. As previously described, coil 60 is a gas-permeable tubing. The tubing selected typically has a relatively high gas permeability. The tubing wall thickness is selected based on a balancing of the tubing's ability to withstand the vacuum forces imposed on the inside of the tubing caused by a peristaltic pump, which is typically used in liquid gas analyzers to move the sample and standard solutions into, out of and through the fluid testing modules, and the speed of gas transfer through the tubing wall and into the calibrating solution passing through coil 60. The number or coil wraps 62 required is also a function of the gas permeability of the tubing used, the wall thickness, the flow rate of the solution through the coil, and the temperature of the mandrel. For example, the number of coil wraps 62 required to insure that the calibration solution passing through coil 60 is fully equilibrated with the gas level within internal space 29 before exiting through solution outlet 52 is dependent on a tubing having a pre-defined gas permeability and a predefined wall thickness where the mandrel is set to a pre-defined temperature and the flow rate of the calibration solution through coil 60 is predefined. For instance, increasing the flow rate would require a greater number of coil wraps 62 to achieve equilibration before the calibration solution exits solution outlet 52. Conversely, decreasing the flow rate would require fewer coil wraps 62. This is so because the solution must reside within coil 60 a sufficient amount of time to permit equilibration the gas within internal space 29 with the liquid in coil 60 as the liquid passes through coil 60 so that the liquid exiting solution outlet 52 can be used as a gas calibration solution. Also, if a tubing is used that has a lesser gas permeability, more coil wraps 62 are required. This is also the case when varying the thickness of the tubing. The thicker the tubing wall, the greater the number of coil wraps 62 and the thinner the tubing wall, the lesser the number of coil wraps 62. The thickness of the tubing wall is restricted to a size such that the tubing internal diameter (I.D.) will not collapse when the fluid within coil 60 is exposed to the vacuum forces created and imposed by a peristaltic pump. The temperature at which the temperature-controlled mandrel 42 is operated also influences the number of coil wraps 62 required. The higher the temperature, the lower the number of coil wraps 62 and the lower the temperature, the higher the number of coil wraps 62. As can be seen, it is a balancing of the various characteristics of the gas-liquid equalizer assembly 10 depending on the factors of more importance to the user such as, for example, quickness of solution equilibration, size of the assembly, preferred temperature, etc., a determination that can be made by one of ordinary skill in the art without undue experimentation. Material that is usable as tubing in the present invention is material having a gas permeability equal to or greater than about $0.6 \times 10^{-13}$ cm³·cm cm⁻² s⁻¹ Pa⁻¹ at 25° C. for a 25 micron film of the material, preferably equal to or greater than about $3 \times 10^{-13}$ cm³·cm cm⁻² s⁻¹ Pa⁻¹, and more preferably equal to or greater than about $7 \times 10^{-13}$ cm³·cm cm⁻² s⁻¹ Pa⁻¹.

The following examples illustrate specific embodiments of the gas-liquid equalizer assembly 10. The following examples used atmospheric oxygen (20.9%) for creating an oxygen calibration solution for a gas liquid analyzer such as a blood gas analyzer. The temperature of the temperature-controlled, thermally-conductive mandrel 42 was set at 37° C. Flow rate of the solution through coil 42 was about 80 microliters per second. Atmospheric pressure was recorded. This information was used to calculate the exact oxygen value of the equilibrated solution exiting solution outlet 64 of gas-liquid equalizer assembly 10.

Example 1

A temperature-controlled, thermally-conductive mandrel 42 having an outer diameter of about 1 inch and a coil 60 of polytetrafluoroethylene (PTFE) tubing having a coil internal diameter of about 1 inch (since it is wrapped around mandrel 42) were used. The PTFE tubing has a gas permeability for oxygen of $7 \times 10^{-13}$ cm³·cm cm⁻² s⁻¹ Pa⁻¹ and a gas permeability for carbon dioxide of $7 \times 10^{-13}$ cm³·cm cm⁻² s⁻¹ Pa⁻¹ at 25° C. for a 5 micron film of PTFE. The following table gives the specific parameters of the gas permeable tubing of the gas equilibration device 40.

TABLE 1

| Tubing Material | Tubing I.D. (inches) | Tubing Wall Thickness (inches) | Tubing O.D. (inches) | Number of Coil Wraps | Total Length of Tubing (in.)* |
|---|---|---|---|---|---|
| PTFE | 0.04 | 0.012 | 0.064 | 22.5 | 72 ± 1.5 |

*Note: Total length includes the connections to solution inlet 64 and solution outlet 66

The target volume size in coil 60 was 1.5 milliliters. The calibration solution exiting at solution outlet 66 was fully equilibrated with atmospheric oxygen in a solution at 37° C. and was usable as an oxygen calibration solution for the liquid gas analyzer.

Example 2

A temperature-controlled, thermally-conductive mandrel 42 having an outer diameter of about 1 inch and a coil 60 of fluorinated ethylene propylene (FEP) tubing having a coil internal diameter of about 1 inch (since it is wrapped around mandrel 42) were used. The FEP tubing has a gas permeability for oxygen of $3 \times 10^{-13}$ cm³·cm cm⁻² s⁻¹ Pa⁻¹ and a gas permeability for carbon dioxide of $10 \times 10^{-13}$ cm³·cm cm⁻² s⁻¹ Pa⁻¹ at 25° C. for a 5 micron film of FEP. The following table gives the specific parameters of the gas permeable tubing of the gas equilibration device 40.

TABLE 2

| Tubing Material | Tubing I.D. (inches) | Tubing Wall Thickness (inches) | Tubing O.D. (inches) | Number of Coil Wraps | Total Length of Tubing (in.)* |
|---|---|---|---|---|---|
| FEP | 0.04 | 0.013 | 0.066 | 22.5 | 72 ± 1.5 |

*Note: Total length includes the connections to solution inlet 64 and solution outlet 66

The target volume size in coil 60 was 1.5 milliliters. The calibration solution exiting at solution outlet 66 was fully equilibrated with atmospheric oxygen in a solution at 37° C. and was usable as a calibration solution for the liquid gas analyzer.

It should be understood that the gas permeability values of PTFE and FEP are based on 25 μm film thickness at 25° C.

It is contemplated that internal space 29 may optionally be equilibrated with an atmosphere containing other gases and/or other gases at other concentration levels. In the case where atmospheric air is not used, the housing must be constructed to be air tight so that a gas or gas mixture in internal space 29 and used for equilibrating with the solution passing through gas-permeable tubing 60 does not get contaminated with air from the atmosphere. The skilled artisan will realize that plurality of openings and/or slots 28 would need to be air tight, the combination of the frame 22 and cover 30 would need to be air tight, and cover 30 would not have any vent openings 32b, 34b or vent openings 32b, 34b would need to be plugged and air tight as well.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A gas-solution equilibrium device for use in a liquid sample gas analyzer comprising:
   a temperature-controlled, thermally-conductive mandrel;
   a coil of gas-permeable tubing wrapped around the mandrel, the gas-permeable tubing having an inlet and an outlet; and
   a housing having an internal space containing the temperature-controlled, thermally-conductive mandrel, the coil of gas-permeable tubing and a volume of gas wherein the coil of gas-permeable tubing has a predefined linear length and the gas-permeable tubing has a predefined wall thickness, the combination of which together is capable of equilibrating a liquid passing through the coil at a predefined flow rate with the gas within the internal space to provide a gas calibration solution in real time at the outlet of the tubing for the liquid gas analyzer.

2. The device of claim 1 wherein the volume of gas is atmospheric air.

3. The device of claim 1 wherein the gas-permeable tubing is made of a material having a relatively high gas permeability for oxygen or carbon dioxide in the range of about $0.6 \times 10^{-13}$ cm³ cm cm⁻² s⁻¹ Pa⁻¹ to about $10 \times 10^{-13}$ cm³ cm cm⁻² s⁻¹ Pa⁻¹.

4. The device of claim 1 wherein the gas-permeable tubing is made of a material having an oxygen permeability selected from the group consisting of equal to or greater than about $0.6 \times 10^{-13}$ cm³ cm cm⁻² s⁻¹ Pa⁻¹, equal to or greater than about $3 \times 10^{-13}$ cm³ cm cm⁻² s⁻¹ Pa⁻¹, and equal to or greater than about $7 \times 10^{-13}$ cm³ cm cm⁻² s⁻¹ Pa⁻¹.

5. The device of claim 1 wherein the gas-permeable tubing is made of a material having an oxygen permeability equal to about $3 \times 10^{-13}$ cm³ cm cm⁻² s⁻¹ Pa⁻¹.

6. The device of claim 1 wherein the gas-permeable tubing is made of a material having an oxygen permeability equal to about $7 \times 10^{-13}$ cm³ cm cm⁻² s⁻¹ Pa⁻¹.

7. The device of claim 1 wherein the gas-permeable tubing is made of a material having an oxygen permeability in the range of about $3 \times 10^{-13}$ cm³ cm cm⁻² s⁻¹ Pa⁻¹ to about $7 \times 10^{-13}$ cm³ cm cm⁻² s⁻¹ Pa⁻¹.

8. The device of claim 1 wherein the gas-permeable tubing has a wall thickness in the range of about 0.011 inches to about 0.014 inches.

9. The device of claim 1 wherein the gas-permeable tubing has a wall thickness in the range of about 0.012 inches to about 0.013 inches.

10. The device of claim 1 wherein the gas-permeable tubing has a wall thickness sufficient to prevent wall collapse when the tubing is subjected to vacuum effect from a peristaltic pump while providing sufficient oxygen permeability to achieve solution oxygen equilibrium with atmospheric oxygen at the solution outlet for a solution passing through the tubing.

11. The device of claim 1 wherein the gas-permeable tubing is made of a material having a carbon dioxide permeability selected from the group consisting of equal to or greater than about $3 \times 10^{-13}$ $cm^3$ cm $cm^{-2}$ $s^{-1}$ $Pa^{-1}$, equal to or greater than about $7 \times 10^{-13}$ $cm^3$ cm $cm^{-2}$ $s^{-1}$ $Pa^{-1}$, and equal to or greater than about $10 \times 10^{-13}$ $cm^3$ cm $cm^{-2}$ $s^{-1}$ $Pa^{-1}$.

12. The device of claim 1 wherein the gas-permeable tubing is made of a material having a carbon dioxide permeability equal to about $3 \times 10^{-13}$ $cm^3$ cm $cm^{-2}$ $s^{-1}$ $Pa^{-1}$.

13. The device of claim 1 wherein the gas-permeable tubing is made of a material having a carbon dioxide permeability equal to about $7 \times 10^{-13}$ $cm^3$ cm $cm^{-2}$ $s^{-1}$ $Pa^{-1}$.

14. The device of claim 1 wherein the gas-permeable tubing is made of a material having a carbon dioxide permeability equal to about $10 \times 10^{-13}$ $cm^3$ cm $cm^{-2}$ $s^{-1}$ $Pa^{-1}$.

15. The device of claim 1 wherein the gas-permeable tubing is made of a material having a carbon dioxide permeability in the range of about $7 \times 10^{13}$ $cm^3$ cm $cm^{-2}$ $s^{-1}$ $Pa^{-1}$ to about $10 \times 10^{-13}$ $cm^3$ cm $cm^{-2}$ $s^{-1}$ $Pa^{-1}$.

16. The device of claim 1 wherein the temperature-controlled, thermally-conductive mandrel has a thin-film heater disposed on an inside wall of the tubular mandrel.

17. The device of claim 1 wherein the gas-permeable tubing has a length in the range of about 35 inches to about 75 inches.

18. The device of claim 17 wherein the perfluoroalkoxy copolymer is tetrafluoroethylene-perfluoro(alkoxy vinyl ether).

19. The device of claim 17 wherein the ethylene-tetrafluoroethylene copolymer is polyethylenetetrafluoroethylene.

20. The device of claim 1 wherein the coil has predefined number of turns in the range of about 11 turns to about 23 turns.

21. The device of claim 1 wherein the gas-permeable tubing is made of a material selected from the group consisting of polytetrafluoroethylene, fluorinated ethylene propylene, perfluoroalkoxy copolymer, and ethylene-tetrafluoroethylene copolymer.

22. A gas-liquid equilibrium coil where the gas-liquid equilibrium coil provides, in real-time, a gas calibrating solution in a gas-liquid analyzer, the gas-liquid equilibrium coil comprising:
a temperature-controlled, thermally-conductive mandrel;
a coil of gas-permeable tubing wrapped around the mandrel, the gas-permeable tubing having an inlet and an outlet; and
temperature and gas means for controlling the environment around the gas-liquid equilibrium coil wherein a gas calibrating solution that exits the gas-liquid equilibrium coil has a predefined gas concentration defined by the temperature and gas of the temperature and means.

23. The equilibrium coil of claim 18 wherein the gas permeable tubing is made of a material having a relatively high gas permeability for oxygen or carbon dioxide in the range of about $3 \times 10^{-13}$ $cm^3$ cm $cm^{-2}$ $s^{-1}$ $Pa^{-1}$ to about $10 \times 10^{-13}$ $cm^3$ cm $cm^{-2}$ $s^{-1}$ $Pa^{-1}$.

* * * * *